US00PP33953P2

(12) United States Plant Patent
Grazzini

(10) Patent No.: US PP33,953 P2
(45) Date of Patent: Feb. 15, 2022

(54) ***DIANTHUS* PLANT NAMED 'G18144'**

(50) Latin Name: *Dianthus hybrida*
Varietal Denomination: G18144

(71) Applicant: Garden Genetics, Bellefonte, PA (US)

(72) Inventor: Richard A. Grazzini, Bellefonte, PA (US)

(73) Assignee: Garden Genetics llc, Bellefonte, PA (US)

( * ) Notice: Subject to any disclaimer, the term of this patent is extended or adjusted under 35 U.S.C. 154(b) by 0 days.

(21) Appl. No.: 17/354,185

(22) Filed: Jun. 22, 2021

(51) Int. Cl.
*A01H 5/02* (2018.01)
*A01H 6/30* (2018.01)

(52) U.S. Cl.
USPC ..... Plt./272
CPC ..... *A01H 6/305* (2018.05)

(58) Field of Classification Search
USPC ..... Plt./272
CPC ..... A01H 6/305; A01H 5/02
See application file for complete search history.

*Primary Examiner* — Keith O. Robinson
(74) *Attorney, Agent, or Firm* — Cassandra Bright

(57) ABSTRACT

A new and distinct cultivar of *Dianthus* plant named 'G18144' is disclosed, characterized by pink flowers with a distinct red eye. Plants are Winter hardy in Zone 5 and flower continuously from May through early November at 41N latitude. Plant growth continues to emerge from the center of the plant, avoiding a bare center. The new variety is a *Dianthus*, normally used for outdoor ornamental purposes.

2 Drawing Sheets

Figure 1:
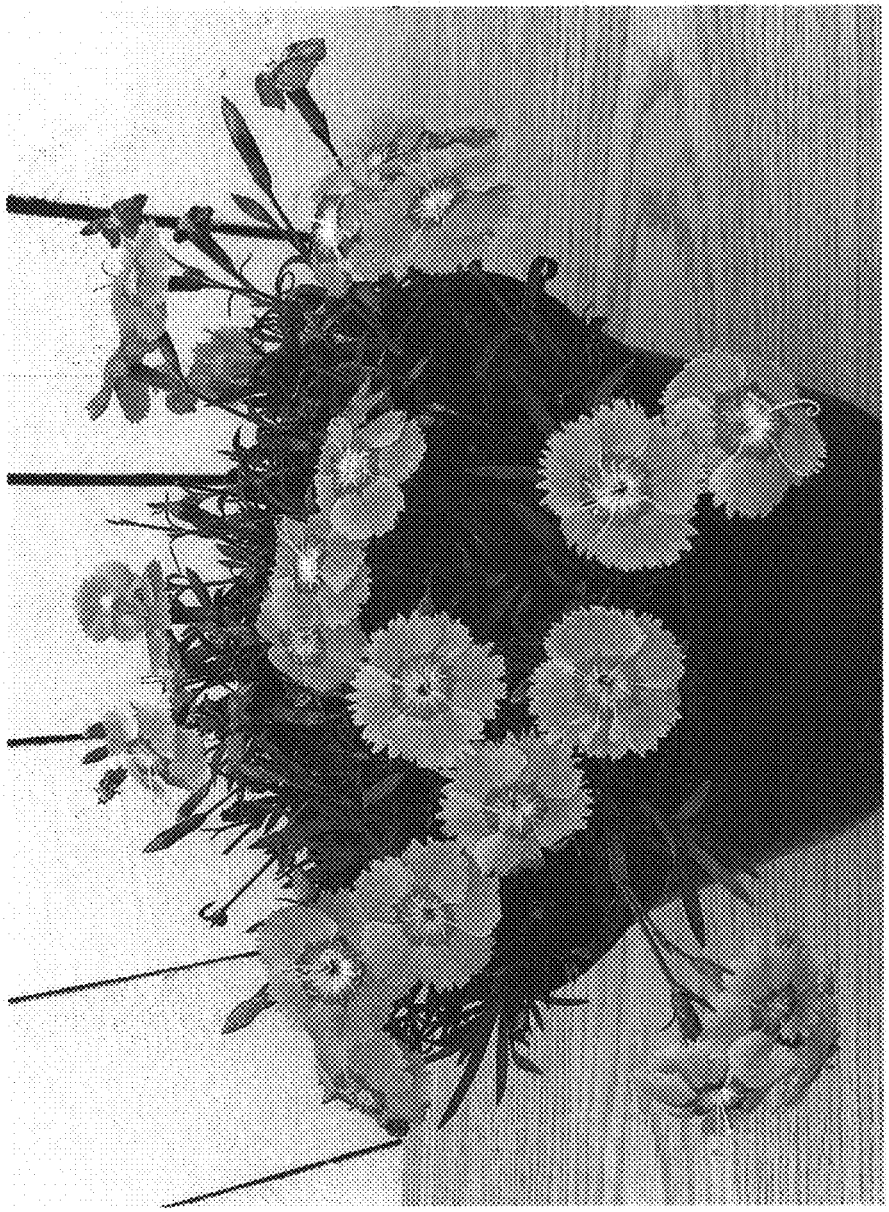

Latin name of the genus and species: *Dianthus hybrida.* Variety denomination: 'G18144'.

BACKGROUND OF THE INVENTION

The new *Dianthus* cultivar is a product of a planned breeding program conducted by the inventor at a research nursery in Bellefonte, Pa. The cross-pollination resulting in this new variety was made during December of 2017.

The seed parent is the unpatented proprietary variety referred to as *Dianthus* 'G17-024'. The pollen parent is the unpatented proprietary variety referred to as *Dianthus* 'G17-022'. The new variety was selected in June of 2018 by the inventor in a group of seedlings resulting from the 2017 cross-pollination, in a nursery in Bellefonte, Pa.

Asexual reproduction of the new cultivar was performed by vegetative cuttings. This was first performed at the same nursery in in Bellefonte, Pa. during July of 2018, and has shown that the unique features of this cultivar are stable and reproduced true to type in multiple successive generations.

SUMMARY OF THE INVENTION

The cultivar 'G18144' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'G18144' These characteristics in combination distinguish 'G18144' as a new and distinct *Dianthus* cultivar:

1. Flowers are pink in color, with a circular red eye, and a variable light-red "blush" on the flower petal.
2. Flowers continuously in a greenhouse under ambient (natural) lighting.

3. Flowers constantly outdoors (in-ground) from late May thru early November at 41N latitude.
4. Large flowers on short peduncles, forming a dense floral canopy just above the foliage.
5. Good winter-hardiness (USDA z5, at least) and good winter survival.
6. Healthy plants and leaves with constant growth from center (does not form bare center "donut" or "birdsnest").
7. Strong field-tolerance to common *Dianthus* pathogens.

PARENT COMPARISON

Plants of the new cultivar 'G18144' are similar to plants of the seed parent in most horticultural characteristics; however, plants of the new cultivar 'G18144' differ in the following:

1. New variety 'G18144 has light pink flowers with a red "eye". Seed parent G17-024 has dark pink flowers with no eye.
2. New variety 'G18144 has glaucous grey-green foliage. Seed parent G17-024 has mid-green leaves.
3. New variety 'G18144 has relatively short peduncles, rising about 2-2.5" above the foliage. Seed parent G17-024 has longer peduncles, about 3.0" above the leaves.
4. New variety 'G18144 flowers continuously under natural light at 41N latitude. Seed parent G17-024 repeat-blooms, cycling in and out of flower under the same conditions.
5. New variety 'G18144' is field-tolerant of common *Dianthus* leaf and crown pathogens. Seed parent G17-024 is not as tolerant, and typically dies out in the center, forming a "donut" of healthy foliage around a dead center.

Plants of the new cultivar 'G18144' are similar to plants of the pollen parent in most horticultural characteristics; however, plants of the new cultivar 'G18144' differ in the following:

1. New variety 'G18144 has light pink flowers with a red "eye". Pollen parent G17-022 has light pink flowers and a dark violet eye.
2. New variety 'G18144' has grey-green foliage. Pollen parent G17-022 has more intense silvery-blue leaves.
3. New variety 'G18144' has short peduncles, rising between 2.0-2.5" above the foliage. Pollen parent G17-022 has much longer peduncles, between 3.5 and 4.0" above the foliage.
4. New variety 'G18144' flowers continuously under natural light at 41N latitude. Pollen parent G17-022 repeat-blooms, cycling in and out of flower under similar conditions.
5. New variety 'G18144' is field-tolerant of common *Dianthus* leaf and crown pathogens. Pollen parent G17-022 is not especially tolerant, and typically dies out in the center, forming a "donut" of healthy foliage around a dead center.

COMMERCIAL COMPARISON

Plants of the new cultivar 'G18144' are comparable to the commercial variety *Dianthus* 'WP 11 TYR04', U.S. Plant Pat. No. 25,077. The two *Dianthus* varieties are similar in most horticultural characteristics, however, the new variety 'G18144' differs in the following;

1. New variety 'G18144' has single, light pink flowers with a uniform, circular medium-red eye. Comparison variety 'WP 11 TYR04' has pink flower petals with a dark red eye which spreads across the petal in lines and splashes.
2. New variety 'G18144' flowers continuously under natural light at 41N latitude. Comparison variety 'WP 11 TYR04' repeat-blooms under similar conditions, but does not bloom continuously.
3. New variety 'G18144' has mid-green foliage. Comparison variety 'WP 11 TYR04' has glaucous grey-green leaves.
4. New variety 'G18-144' has relatively short peduncles, rising 2.0-2.5" above the foliage. Comparison variety 'WP 11 TYR04' has slightly longer peduncles, rising about 3.0" above the leaves.

Plants of the new cultivar 'G18144' are comparable to the commercial variety *Dianthus* 'Uribest52', U.S. Plant Pat. No. 28,239. The two *Dianthus* varieties are similar in most horticultural characteristics; however, the new variety 'G18144' differs in the following;

1. New variety 'G18144' has single, light pink flowers. Comparison variety 'Uribest52' has deep red-purple flowers.
2. Flowers of variety 'G18144' have a uniformly circular medium-red eye. Comparison variety 'Uribest52' has no eye in its flowers.
3. New variety 'G18144' has large single flowers, between 1.5 and 2.0" in diameter. Comparison variety 'Uribest52' has relatively small flowers (ca. 1.0") in comparison.
4. New variety 'G18144' has longer peduncles, with flower placement between 2.0-2.5" above the leaves. Comparison variety 'Uribest52' has much shorter peduncles (1.5-2.0"), with the flowers displayed very close to the foliage canopy.

BRIEF DESCRIPTION OF THE PHOTOGRAPHS

The accompanying photograph in FIG. 1 illustrates a typical flowering plant of 'G18144' grown outdoors in Bellefonte, Pa. at approximately 4 months old in a 1 gallon pot.

Figure 2:
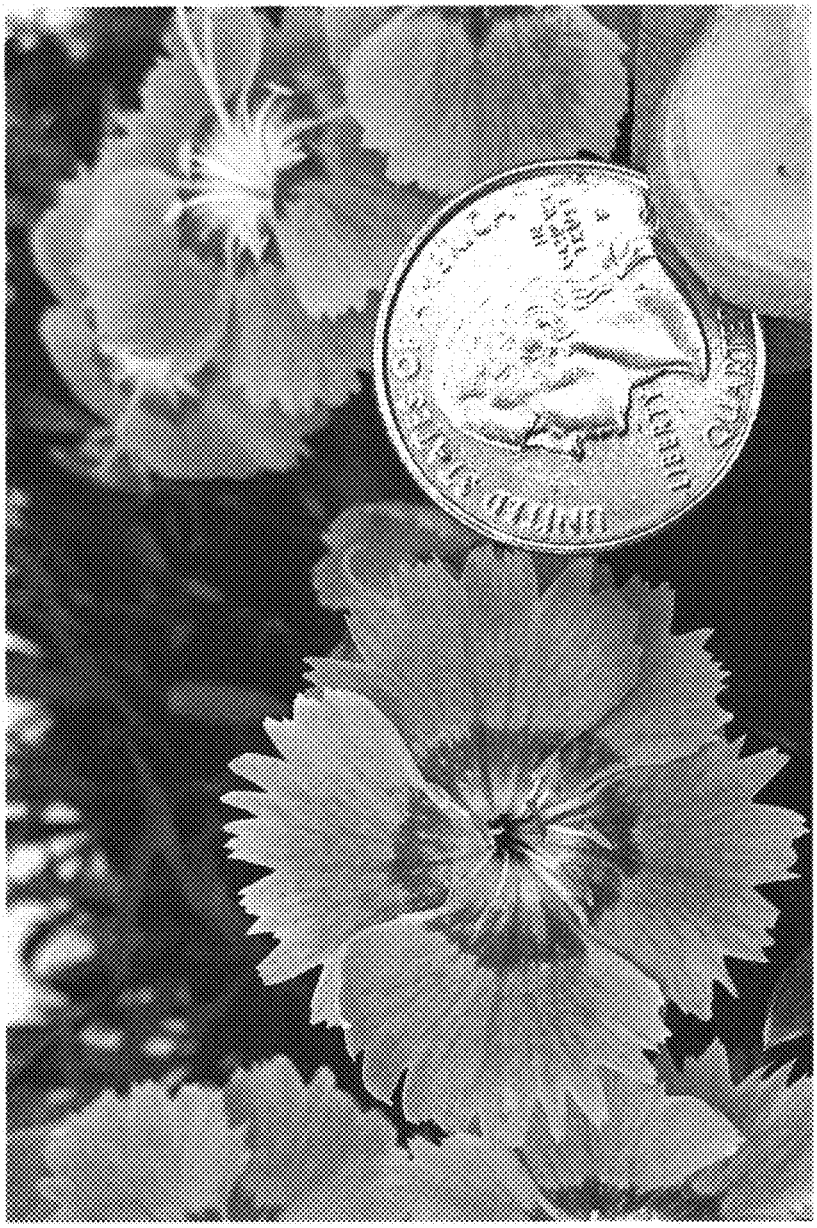

FIG. 2 illustrates a close-up view of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'G18144' plants grown outdoors in Camarillo, Calif. The growing temperature ranged from approximately 10° C. to 25° C. during the day and from approximately 6° C. to 12° C. during the night. General light conditions are normal sunlight and numerical values represent averages of typical plant types. Measurements were taken during June of 2021.

Botanical classification: *Dianthus hybrida* 'G18144'.

PROPAGATION

Time to initiate roots: About 10 days at approximately 24° C.

Time to produce a rooted cutting: About 18 days at 24° C.

Root description: Fibrous roots, approximately 1 to 3 mm in diameter, colored near Orange-White 159C. measured with R.H.S. Chart.

PLANT

Age of plant described: About 6 weeks from a rooted cutting.

Growth habit: Mounded flowering perennial.

Plant spread: About 15 cm.

Plant height: About 8 cm.

Plant vigor: Strong.

Length plant stem: Average 6 cm.

Diameter of plant stem: Approximately 3 mm.

Quantity stems: Approximately 30 to 40.

Stem:

*Color*.—Near RHS Green 137B.

*Texture*.—Smooth.

*Hollowness*.—Slightly hollow with age.

Internode length: 1 to 2 cm.

FOLIAGE

Leaf:

*Arrangement*.—Opposite (in pairs).

*Quantity*.—Approximately 12 to 16 fully expanded per stem.

*Average length*.—2.5 to 4.0 cm.

*Average width*.—3 mm.

*Shape of blade*.—Linear.

*Apex*.—Acute.

*Base*.—Clasping.

*Attachment*.—Sessile.

*Margin*.—Entire.

*Texture of top surface*.—Smooth.

*Texture of bottom surface*.—Smooth.

*Pubescence*.—None.

*Color*.—Young foliage upper side: Near RHS Green 137A. Young foliage under side: Near RHS Green 137B. Mature foliage upper side: Near RHS Green 139B. Mature foliage under side: Near RHS Green 139C.

*Venation*.—Type: Linear. Venation color upper side: Indistinguishable from foliage. Venation color under side: Indistinguishable from foliage.

FLOWER

Natural flowering season: May through early November at 41N latitude.

Inflorescence type and habit: Umbel of 2 to 4 flowers.

Flower longevity on plant: Individual flowers about 10 days.

Quantity of flowers: Approximately 25 flowers and buds on a 6-week old plant.

Flowers persistent or self-cleaning: Persistent.

Fragrance: Faint sweet scent.

Inflorescence (umbel) size:

*Diameter*.—Approximately 6.0 cm.

*Height*.—Approximately 5.0 cm.

Individual flower size:

*Diameter*.—Approximately 3.0 cm.

*Length*.—Approximately 2.8 cm.

Petals:

*Petal arrangement*.—Single overlapping whorl.

*Shape*.—Spatulate, elongated base.

*Base*.—Long attenuate.

*Margin*.—Serrated.

*Apex*.—Serrate.

*Length*.—Upper section, outside of tube: 1.5 cm. Elongated base, in tube, 1.8 cm.

*Width*.—Upper section, outside of tube: 1.5 cm. Elongated base, in tube, 3 mm.

*Petal quantity*.—Average range 12 to 18.

*Texture*.—Smooth all surfaces.

*Aspect*.—Nearly flat.

Color:

*When opening*.—Upper surface: Near RHS Red-Purple 73A, flushed 72C. Center eye Red 46B, visible throat near 73D. Lower surface: Near RHS Red-Purple N74D. Base near tube 73D.

*Fully opened*.—Upper surface: Near RHS Red-Purple 73A, flushed N74B. Center eye Red 46B, visible throat near 73D. Lower surface: Near RHS Red-Purple N74D. Base near tube 73D.

Tube:

*General description*.—Tube consists of the elongated, unfused base of the petals. Tube shape caused by a fused calyx.

*Length*.—1.8 cm.

*Width*.—5 mm.

*Texture*.—Smooth.

Color:

*Fully opened*.—Inner surface: Near RHS Green 138A. Outer surface: Near RHS Green 139D.

Bud:

*Shape*.—Elongated cylinder.

*Length*.—Average 2.0 cm.

*Diameter*.—Average 1.0 cm.

*Color*.—Appearing petals colored near Red-Purple N74C 54D flushed Red-Purple N74A.

Sepals:

*Quantity*.—5.

*Arrangement*.—Fused tube.

*Shape*.—Cylindric.

*Length*.—1.5 cm.

*Width*.—0.3 cm.

*Margin*.—Entire.

*Apex*.—Acute.

*Texture*.—Smooth upper and lower surfaces.

*Color*.—Near RHS Green 138B.

Bracteoles:

*Shape*.—Narrow Deltoid.

*Quantity per flower*.—5-7.

*Length*.—Average 5 mm.

*Width*.—Average 4 mm.

*Margin*.—Entire.

*Texture*.—Smooth.

*Color*.—Near RHS Green 138A.

Peduncle:

*Length*.—Average 2 cm.

*Diameter*.—2.0 mm.

*Color*.—Near RHS Green 138A.

*Orientation*.—Upright.

*Strength*.—Moderate.

*Texture*.—Smooth.

REPRODUCTIVE ORGANS

Stamens:

*Number*.—About 10.

*Filament length*.—1.5 cm.

*Filament color*.—Near White 155D.

Anthers:

*Shape*.—Linear.

*Length*.—3 mm.

*Color*.—Red-Purple N74D.

*Pollen*.—Not observed.

Pistil:

*Number*.—1, 2 stigmas.

*Length*.—2.5 cm.

*Style*.—Number: 2. Length: Approximately 1.7 cm. Color: Base near White N155C, upper-section Red-Purple 73D.

*Stigma*.—Shape: Linear. Color: Near RHS Red-Purple N74D.

*Ovary*.—Shape: Oblong. Diameter: 7 mm. Length: 7 mm. Color: Near RHS Near RHS Yellow-Green 150D.

OTHER CHARACTERISTICS

Fruits and seeds: Not observed to date.

Disease/pest resistance: Shows good field-tolerance to common *Dianthus* pathogens. Specific pathogens resistance have not been determined.

Temperature range: Winter hardiness to at least USDA Zone 5.

What is claimed is:

1. A new and distinct cultivar of *Dianthus* plant named 'G18144' as herein illustrated and described.

* * * * *